(12) United States Patent
Tani et al.

(10) Patent No.: US 10,098,858 B2
(45) Date of Patent: Oct. 16, 2018

(54) AQUEOUS LOXOPROFEN-CONTAINING PATCHES

(75) Inventors: Kazuha Tani, Sanuki (JP); Mitsuji Akazawa, Higashikagawa (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 1102 days.

(21) Appl. No.: 12/747,644

(22) PCT Filed: Dec. 11, 2008

(86) PCT No.: PCT/JP2008/072508
§ 371 (c)(1),
(2), (4) Date: Sep. 20, 2010

(87) PCT Pub. No.: WO2009/075324
PCT Pub. Date: Jun. 18, 2009

(65) Prior Publication Data
US 2011/0003893 A1    Jan. 6, 2011

(30) Foreign Application Priority Data

Dec. 12, 2007 (JP) ................................ 2007-320530

(51) Int. Cl.
*A61K 31/192* (2006.01)
*A61K 9/70* (2006.01)

(52) U.S. Cl.
CPC .......... *A61K 31/192* (2013.01); *A61K 9/7061* (2013.01)

(58) Field of Classification Search
USPC ....................................................... 514/547
See application file for complete search history.

(56) References Cited

U.S. PATENT DOCUMENTS

| | | | |
|---|---|---|---|
| 4,814,173 A | 3/1989 | Song et al. | |
| 4,908,389 A | 3/1990 | Mahjour et al. | |
| 5,478,567 A * | 12/1995 | Nakagawa et al. | 424/449 |
| 5,496,819 A * | 3/1996 | Okuyama et al. | 514/226.5 |
| 5,601,839 A | 2/1997 | Quan et al. | |
| 6,248,350 B1 | 6/2001 | Mori et al. | |
| 7,018,647 B1 * | 3/2006 | Yamasaki et al. | 424/449 |
| 2003/0149383 A1 * | 8/2003 | Ikeura et al. | 602/8 |
| 2007/0189978 A1 * | 8/2007 | Zhang et al. | 424/45 |
| 2007/0280980 A1 | 12/2007 | Hashimoto et al. | |
| 2008/0113010 A1 | 5/2008 | Yama et al. | |

FOREIGN PATENT DOCUMENTS

| | | |
|---|---|---|
| EP | 0 255 485 A2 | 2/1988 |
| JP | 63-99008 A | 4/1988 |
| JP | 63-126832 A | 5/1988 |
| JP | 10-120560 A | 5/1998 |
| JP | 10-507199 A | 7/1998 |
| JP | 2004-83579 A | 3/2004 |
| WO | WO 01/17526 A1 | 3/2001 |
| WO | WO 2005/110482 A1 | 11/2005 |
| WO | WO 2006/048939 A1 | 5/2006 |

OTHER PUBLICATIONS

Iwakura, S. et al., "Effect of Water-Holding Capacity of Molded Cataplasm on Drug Release Performance and Adhesiveness", Therapeutic Research, 1985, pp. 969 to 973, vol. 3, No. 6. (Ten (10) pages including English translation).
International Search Report dated Jan. 20, 2009 (Two (2) pages).

* cited by examiner

*Primary Examiner* — Jennifer A Berrios
(74) *Attorney, Agent, or Firm* — Crowell & Moring LLP

(57) ABSTRACT

An aqueous loxoprofen-containing patch is provided, which has good stability and excellent transdermal absorption of loxoprofen. The aqueous patch includes loxoprofen or a salt thereof and triacetin. Specifically, the aqueous patch includes, based on the weight of the adhesive gel base, 0.1 to 5% by weight of loxoprofen or a salt thereof, 0.5 to 5% by weight of triacetin, 1 to 30% by weight of a water-soluble polymer, 0.01 to 5% by weight of a cross-linking agent, 10 to 90% by weight of purified water, and 0 to 20% by weight of an inorganic powder.

2 Claims, 1 Drawing Sheet

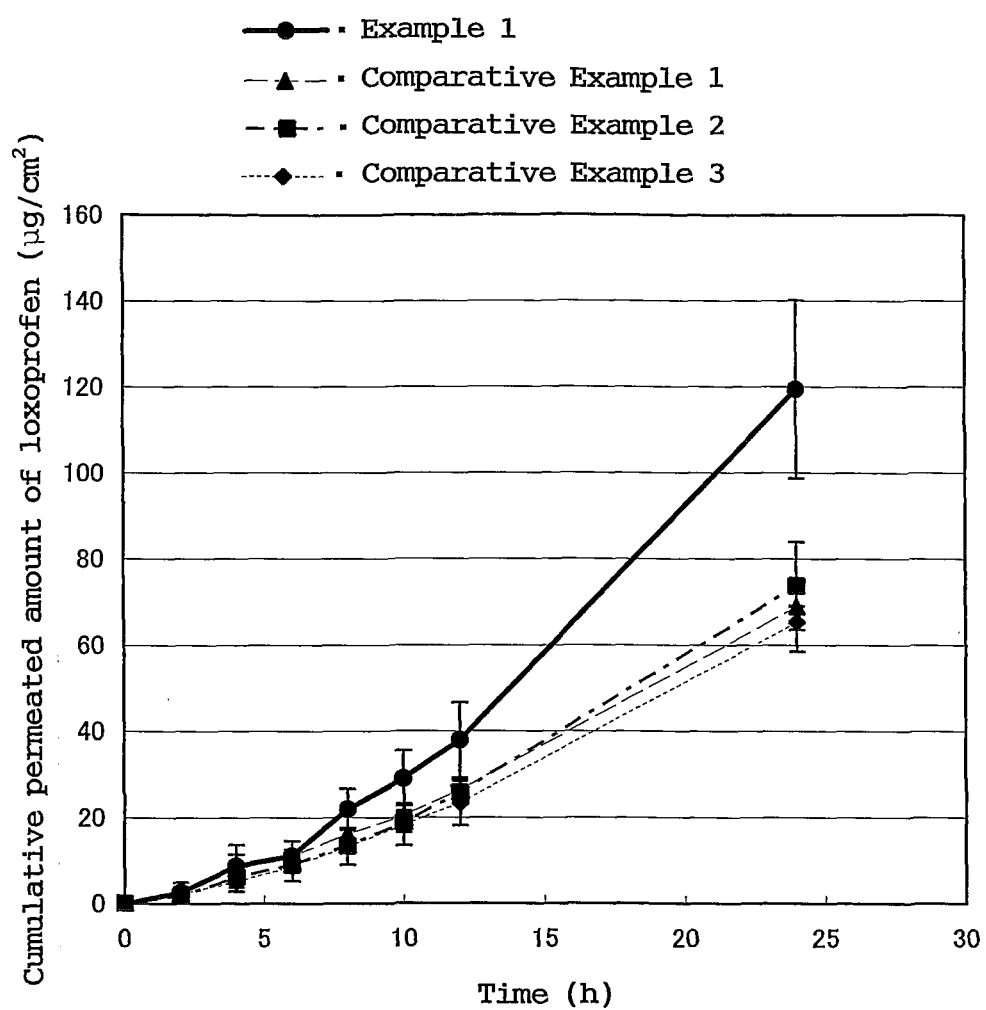

AQUEOUS LOXOPROFEN-CONTAINING PATCHES

This application is a national stage of PCT International Application No. PCT/JP2008/072508, filed Dec. 11, 2008, which claims priority under 35 U.S.C. § 119 to Japanese Patent Application No. 2007-320530, filed Dec. 12, 2007, the entire disclosure of which is herein expressly incorporated by reference.

TECHNICAL FIELD

The present invention relates to aqueous loxoprofen-containing patches which have good stability in the preparation and excellent transdermal absorption of loxoprofen.

BACKGROUND ART

Loxoprofen has an excellent medicinal effect as a non-steroidal anti-inflammatory analgesic agent derived from phenylpropionic acid and has been widely used as an oral medicine. Some external preparations contain loxoprofen are also proposed. For example, Patent Document 1 discloses a patch comprising loxoprofen and crotamiton as a loxoprofen-containing patch.

The above patent is aimed at providing a loxoprofen-containing patch which has high pharmaceutical stability and reduced skin irritation by blending crotamiton with the aqueous base for the patch to increase solubility of loxoprofen in the preparation; however, sufficient transdermal absorption of loxoprofen as an active ingredient was not achieved.

[Patent Document 1] Japanese Patent Application Laid-Open No. Hei 10-120560

Accordingly, there is currently a demand for further improved external loxoprofen-containing patches which have high stability in the preparation and excellent transdermal absorption of loxoprofen.

DISCLOSURE OF THE INVENTION

Problems to be Solved by the Invention

In view of the above present circumstances, it is an object of the present invention to provide an aqueous loxoprofen-containing patch which has good pharmaceutical stability and excellent transdermal absorption of loxoprofen.

As a result of dedicated research to solve the above problem, the present inventors have newly discovered that patches which have good stability and excellent transdermal absorption of loxoprofen could be provided by dissolving loxoprofen or a salt thereof in an adhesive gel base comprising triacetin such that loxoprofen is dissolved stably in the adhesive gel base, and thus completed the present invention.

Means for Solving the Problems

Therefore, the basic embodiment of the present invention is an aqueous patch comprising loxoprofen or a salt thereof and triacetin.

More specifically, the present invention provides an aqueous patch comprising 0.1 to 5% by weight of loxoprofen or a salt thereof based on the weight of the adhesive gel base and 0.5 to 5% by weight of triacetin based on the weight of the adhesive gel base.

Even more specifically, the present invention provides an aqueous patch comprising, based on the weight of the adhesive gel base, 0.1 to 5% by weight of loxoprofen or a salt thereof, 0.5 to 5% by weight of triacetin, 1 to 30% by weight of a water-soluble polymer, 0.01 to 5% by weight of a cross-linking agent, 10 to 90% by weight of purified water, and 0 to 20% by weight of an inorganic powder.

Effects Of The Invention

In the aqueous patch provided by the present invention, blending loxoprofen or a salt thereof with a base comprising triacetin enabled stable dissolution of loxoprofen in the adhesive gel base.

This stable solubility made it possible to provide an aqueous patch which has excellent transdermal absorption and good pharmaceutical stability of loxoprofen, which conventional aqueous loxoprofen-containing patches had not successfully had.

BRIEF DESCRIPTION OF THE DRAWINGS

FIG. 1 is a graph showing the amount of loxoprofen which permeated the skin as measured by the in vitro skin permeation test in Test Example 1.

BEST MODE FOR CARRYING OUT THE INVENTION

Examples of loxoprofen or salts thereof which are used as active ingredients in the aqueous patches of the present invention include: alkali metal salts such as sodium salts, potassium salts, and lithium salts; alkaline earth metal salts such as calcium salts and magnesium salts; metallic salts such as aluminum salts, iron salts, zinc salts, copper salts, nickel salts, and cobalt salts; ammonium salts; amine salts including organic salts such as t-octyl amine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzyl ethylenediamine salts, chloroprocaine salts, procaine salts, diethanolamine salts, N-benzyl-phenethyl amine salts, piperazine salts, tetramethyl ammonium salts, and tris(hydroxymethyl)amino-methane salts; and amino acid salts such as glycine salts, lysine salts, arginine salts, orthinine salts, glutamates, and aspartates. Preferably, water-soluble salts are used, and more preferably, sodium salts are used.

The amount of loxoprofen or a salt thereof contained in the aqueous patch provided by the present invention is not limited as long as formulation is possible, though preferably the amount is within the range of 0.1 to 5% by weight, and more preferably 0.5 to 2% by weight, based on the weight of the adhesive gel base.

Less than 0.1% by weight of loxoprofen or a salt thereof in the preparation will result in small transdermal absorption and no desired anti-inflammatory analgesic effect. On the other hand, more than 5% by weight of loxoprofen or salt thereof in the preparation is not preferable, as it causes problems such as its crystallization in the preparation and reduced pharmaceutical availability of the preparation.

It is a feature of the present invention to provide patches which have good stability and excellent transdermal absorption of loxoprofen by dissolving loxoprofen or a salt thereof in the adhesive gel base comprising triacetin such that loxoprofen is dissolved stably in the adhesive gel base.

The triacetin acts as a solvent for loxoprofen or salt thereof.

The amount of triacetin in the present invention may range from 0.5 to 5% by weight, preferably 1 to 2% by weight based on the weight of the adhesive gel base. Less than 0.5% by weight of triacetin will result in an insufficient dissolution of loxoprofen or a salt thereof in the adhesive gel base and high transdermal absorption will not be achieved. On the other hand, more than 5% by weight of triacetin will exert unfavorable effects on the physical property of the preparation such as adhesive gel base remaining on the skin surface after the removal of the patch.

Other various bases used in conventional aqueous patches may be used in the aqueous patch provided by the present invention, provided that they do not influence other properties of the preparation.

Such bases include, but not limited to, for example conventional materials, for example, water-soluble polymers such as sodium polyacrylate, polyacrylic acid, carboxy vinyl polymer, sodium carboxymethylcellulose, polyvinyl alcohol, and gelatin; polyalcohols such as glycerin, propylene glycol, and polyethylene glycol; cross-linking agents such as aluminum hydroxide, aluminum potassium sulfate, and aluminum glycinate; inorganic powders such as kaolin and titanium oxide; pH adjusters such as citric acid and tartaric acid; surfactants such as polyoxyethylene sorbitan monooleate, sorbitan monooleate, polyoxyethylene monooleate, glycerol esters of fatty acids, polyglycerol fatty acid esters, polyoxyethylene fatty acid esters, sorbitan esters of fatty acid, polyoxyethylene sorbitan fatty acid esters, polyoxyethylene sorbit fatty acid esters, polyoxyethylene hydrogenated caster oil, and polyoxyethylene alkyl ethers; and purified water.

In addition, absorption enhancers, antiseptics, antioxidants, flavoring agents, coloring agents and the like may be added if necessary.

Each component, particularly in the aqueous patch provided by the present invention, was found to be preferably blended in the base in the following amount: 1 to 30% by weight of a water-soluble polymer, 1 to 50% by weight of a polyalcohol, 0.01 to 5% by weight of a cross-linking agent, 10 to 90% by weight of purified water, and 0 to 20% by weight of an inorganic powder.

Flexible materials such as woven fabrics, nonwoven fabrics, films, and sheets may be used, without particular limitations, as a backing layer for the aqueous patch of the present invention. For example, woven fabrics or nonwoven fabrics made from fibers such as rayon, polyesters, polyolefins, and urethanes or polymer films, foam sheets and the like are used.

Especially preferably, backing layers having elasticity in every direction are used.

Various plastic films may be used as a release sheet to cover the surface of the adhesive gel base serving as an adhesive base.

Examples of such plastic films can include polyethylene, polypropylene, and polyester films, as well as those made from them by subjecting it to mold-release treatment using silicone.

The method for producing the aqueous patch provided by the present invention is not limited to specific methods. As a non-limiting example, in the embodiment where loxoprofen sodium is used as loxoprofen or a salt thereof, a desired aqueous patch can be produced by dissolving the loxoprofen sodium in water, adding the solution to a previously prepared mixed solution consisting of a polyalcohol such as concentrated glycerin, a water-soluble polymer such as polyacrylic acid, an inorganic powder, and purified water, stirring the mixture well, then adding to the mixture triacetin, a pH adjuster, a surfactant, a cross-linking agent and the like, mixing it again well to produce an adhesive gel base, spreading the obtained adhesive gel base onto a backing layer and covering the surface of the adhesive gel base with a plastic film.

The obtained patch of the present invention is cut into pieces of an appropriate size and stored in a container, for example, an air-tight container as necessary.

EXAMPLE

Hereinbelow, the present invention will be described in more detail with reference to Examples, but it is not limited thereto.

Unless otherwise specified, the amount of components is shown in "% by weight" in Examples and Comparative Examples.

Examples 1 to 4

The aqueous patch of the present invention was produced in accordance with the above method for making it based on the formulation described in Table 1 below.

Comparative Example 1

A commercially available Loxonin Pap 100 mg (produced and sold by Lead Chemical Co., Ltd.), was used. The formulation for the commercially available Loxonin Pap is based on that described in Patent Document 1.

Comparative Examples 2 and 3

The aqueous patches of Comparative Examples were produced based on the formulation described in Table 1 below by the above method for producing them.

A patch comprising no triacetin is produced in Comparative Example 2 and a patch comprising crotamiton instead of triacetin is produced in Comparative Example 3.

TABLE 1

| Components | Examples | | | | Comparative Examples | |
|---|---|---|---|---|---|---|
| (% by weight) | 1 | 2 | 3 | 4 | 2 | 3 |
| Loxoprofen sodium | 1.134 | 1.134 | 1.134 | 1.134 | 1.134 | 1.134 |
| Glycerin | 35 | 35 | 35 | 35 | 35 | 35 |
| Sodium polyacrylate | 5 | 5 | 5 | 5 | 5 | 5 |
| Carmellose sodium | 4 | 4 | 4 | 4 | 4 | 4 |
| Hydroxypropylcellulose | 1 | 1 | 1 | 1 | 1 | 1 |
| D-sorbitol | 14 | 14 | 14 | 14 | 14 | 14 |
| Disodium edetate | 0.06 | 0.06 | 0.06 | 0.06 | 0.06 | 0.06 |
| Dihydroxyaluminum aminoacetate | 0.07 | 0.07 | 0.07 | 0.07 | 0.07 | 0.07 |
| Propylene glycol | 3 | 3 | 3 | 3 | 3 | 3 |
| Methylparaben | 0.1 | 0.1 | 0.1 | 0.1 | 0.1 | 0.1 |
| Propylparaben | 0.05 | 0.05 | 0.05 | 0.05 | 0.05 | 0.05 |

TABLE 1-continued

| Components (% by weight) | Examples | | | | Comparative Examples | |
|---|---|---|---|---|---|---|
| | 1 | 2 | 3 | 4 | 2 | 3 |
| Tartaric acid | 0.5 | 0.5 | 0.5 | 0.5 | 0.5 | 0.5 |
| Triacetin | 2 | 0.5 | 5 | 2 | | |
| Crotamiton | | | | | | 2 |
| Polyacrylic acid aqueous solution (20%) | 20 | 20 | | | | |
| Partially neutralized polyacrylate solution | | | 20 | 20 | 20 | 20 |
| Purified water | 14.086 | 15.586 | 11.086 | 13.086 | 16.086 | 14.086 |
| Surfactant | | | | 1 | | |
| Total | 100 | 100 | 100 | 100 | 100 | 100 |

Test Example 1

In Vitro Skin Permeation Test of Aqueous Loxoprofen-Containing Patches

In vitro skin permeation tests using rat skin for the patches of Example 1 and Comparative Examples 1 to 3 were performed.

Skin was excised from the depilated back of a male rat (a Wistar strain, 7-week old) and fixed to a vertical diffusion cell for a permeation test kept at 37° C. Test patches were applied to the corneum side of the excised skin and 10 mL of phosphate buffered saline was added to the inside (dermis layer side) of the excised skin as receiver solution. Subsequently, receiver solution samples were collected over time and the amount of loxoprofen that permeated the excised skin was determined by liquid chromatography.

The results are shown in FIG. 1.

As is understood from the results shown in FIG. 1, the patch of Example 1 showed approximately 1.8 times higher skin permeability than the patch of Comparative Example 2 comprising no triacetin.

Also, the patch of Example 1 showed approximately 1.7 times higher skin permeability than the patch of Comparative Example 3 comprising 2% by weight of crotamiton.

Thus, it is understood that the patch of the present invention shows better permeability of loxoprofen in comparison with the patches of Comparative Examples.

Test Example 2

Stability Test of Aqueous Loxoprofen-Containing Patches

The patches of Example 1 and Comparative Examples 2 and 3 were placed in aluminum bags, hermetically sealed up, and stored for one month at 40° C. The change of the amount of loxoprofen contained in each of these patches was determined by liquid chromatography.

The results are shown in Table 2 below.

The results were expressed as a percentage of the initial weight, with the amount of loxoprofen contained in the patch at the beginning of storing set to 100%.

The mark "*" denotes that crystals of loxoprofen precipitated in the adhesive gel base.

TABLE 2

| | Initial value | one month at 40° C. |
|---|---|---|
| Example 1 | 100 | 98.3 |
| Comparative Example 2 | 100 | 97.7* |
| Comparative Example 3 | 100 | 97.2 |

As is understood from the results shown in Table 2, the patch of Example 1 of the present invention showed a better stability of loxoprofen in the adhesive gel base than the patches of Comparative Examples.

INDUSTRIAL APPLICABILITY

As described above, in the aqueous patch provided by the present invention, loxoprofen is dissolved stably in the adhesive gel base by mixing loxoprofen or a salt thereof into a base comprising triacetin. Thereby, there are provided aqueous patches which have excellent transdermal absorption and good pharmaceutical stability of loxoprofen, which conventional aqueous loxoprofen-containing patches have not successfully had.

The invention claimed is:

1. An aqueous patch comprising an adhesive aqueous gel base comprising a non-steroidal anti-inflammatory analgesic (NSAID) and a single solvent, wherein the NSAID consists of loxoprofen or a salt thereof in an amount of 0.1 to 5% by weight based on a weight of an adhesive gel base and the solvent consists of triacetin in an amount of 0.5 to 5% by weight based on a weight of an adhesive gel base, wherein the triacetin acts as a solvent to dissolve the loxoprofen or a salt thereof.

2. The aqueous patch according to claim 1, further comprising, based on the weight of the adhesive gel base, a water-soluble polymer in an amount of 1 to 30% by weight, a cross-linking agent in an amount of 0.01 to 5% by weight, purified water in an amount of 10 to 90% by weight, and an inorganic powder in an amount of 0 to 20% by weight.

* * * * *